United States Patent [19]

Matsumoto et al.

[11] 4,351,846
[45] Sep. 28, 1982

[54] 3-HYDROXY AND 3-OXO-PROSTAGLANDIN ANALOGUES

[75] Inventors: Kimiichiro Matsumoto; Hajimu Miyake; Hisashi Suga, all of Takatsuki, Japan

[73] Assignee: Ono Pharmaceutical Co., Ltd., Osaka, Japan

[21] Appl. No.: 262,209

[22] Filed: May 8, 1981

[30] Foreign Application Priority Data

May 12, 1980 [JP] Japan .................. 55-061728

[51] Int. Cl.$^3$ .................. C07C 177/00; A61K 31/557
[52] U.S. Cl. .................. 424/305; 536/103; 542/426; 556/441; 560/53; 560/118; 560/121; 562/463; 562/500; 562/503; 424/308; 424/317
[58] Field of Search .................. 560/121, 118, 53; 562/503, 500, 463; 536/103; 542/426; 556/441; 424/305, 317, 308

[56] References Cited

U.S. PATENT DOCUMENTS

| | | | |
|---|---|---|---|
| 4,181,808 | 1/1980 | Johnson | 560/121 |
| 4,205,178 | 5/1980 | Aken | 560/121 |
| 4,260,805 | 4/1981 | Floyd | 560/118 |

Primary Examiner—Robert Gerstl
Attorney, Agent, or Firm—Stevens, Davis, Miller & Mosher

[57] ABSTRACT

Prostaglandin analogues of the formula:

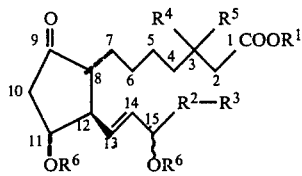

[wherein $R^1$ represents hydrogen or alkyl of 1 to 12 carbon atoms, $R^2$ represents a single bond or alkylene of from 1 to 5 carbon atoms, $R^3$ represents hydrogen, alkyl or alkoxy of 1 to 8 carbon atoms, cycloalkyl or cycloalkyloxy of 4 to 7 carbon atoms unsubstituted or substituted by alkyl of 1 to 8 carbon atoms, or phenyl or phenoxy unsubstituted or substituted by halogen, trifluoromethyl or alkyl of 1 to 4 carbon atoms, one of $R^4$ and $R^5$ represents hydrogen and the other represents hydroxy or $R^4$ and $R^5$ together represent oxo, $R^6$ represents hydrogen or a hydroxy-protecting group which may be removed under acidic conditions, the double bond between the carbon atoms in positions 13 and 14 is trans, the wavy line ⁓ attached to the carbon atom in position 15 represents α- or β- configuration or a mixture thereof and, when one of $R^4$ and $R^5$ represents hydrogen and the other represents hydroxy, the configuration of the carbon atom in position 3 is R— or S or a mixture thereof, provided that, when $R^2$ represents a single bond, $R^3$ does not represent alkoxy, cycloalkyloxy or phenoxy and when $R^6$ represents a hydrogen atom, cyclodextrin clathrates thereof and, when $R^1$ represents a hydrogen atom, non-toxic salts thereof, possess selective prostaglandin-like properties.

22 Claims, No Drawings

3-HYDROXY AND 3-OXO-PROSTAGLANDIN ANALOGUES

DESCRIPTION

This invention is concerned with new prostaglandin analogues.

Prostaglandins are derivatives of prostanoic acid which has the following formula:

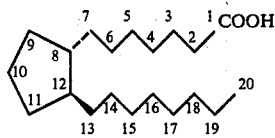

Various types of prostaglandins are known, the types depending inter alia on the structure and substituents on the alicyclic ring. For example, the alicyclic ring of prostaglandin E(PGE) has the structure:

The dotted lines in the foregoing formulae and in other formulae throughout this specification denote, in accordance with generally accepted rules of nomenclature, that the attached grouping lies behind the general plane of the ring system, i.e. that the grouping is in α-configuration, the thickened lines ⮦ denote that the grouping lies in front of the general plane of the system, i.e. that the grouping is in β-configuration, and the wavy line ⁓ indicates that the grouping is in α-or β-configuration.

Such compounds are sub-classified according to the position of double bond(s) in the side chain(s) attached to the 8- and 12-positions of the alicyclic ring. Thus $PG_1$ compounds have a trans-double bond between $C_{13}$-$C_{14}$(trans-$\Delta^{13}$) and $PG_2$ compounds have a cis-double bond between $C_5$-$C_6$ and a trans-double bond between $C_{13}$-$C_{14}$(cis-$\Delta^5$, trans-$\Delta^{13}$). For example, prostaglandin $E_1$ ($PGE_1$) is characterised by the following structure III:

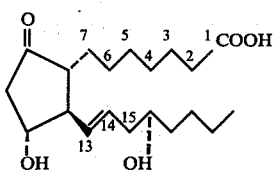

Moreover, when one or more methylene groups are eliminated from the aliphatic group attached to the 12-position of the alicyclic ring of the prostaglandins the compounds are known, in accordance with the usual rules of organic nomenclature, as nor-prostaglandins and, when more than one methylene group is eliminated, the number is indicated by di-, tri- etc, before the prefix "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGE's have a stimulating effect on smooth muscle and increase the intestinal peristalsis; these actions indicate therapeutic utility on post-operative ileus and as purgatives. PGE's may also be used as oxytocics, as abortifacients in the first and second trimesters; in the post-labour abortion of the placenta, and as oral contraceptives because they regulate the sexual cycle of female mammals. PGE's have vasodilator and diuretic activities. They are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the "natural" prostaglandins or one or more of such properties to an enhanced degree, or hitherto unknown pharmacological properties. It has now been found, after research and experimentation, that by introducing a hydroxy group or an oxo group at the 3-position carbon atom of prostaglandin E and certain analogues thereof, new prostaglandin E analogues are obtained which possess the pharmacological properties of the "natural" prostaglandins and are, in some aspects of their activities, an improvement, for example possessing an enhanced strength of activity and/or greater selectivity.

The present invention accordingly provides the new prostaglandin E analogues of the general formula:

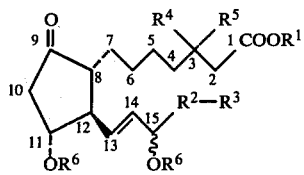

[wherein $R^1$ represents a hydrogen atom or an alkyl group containing from 1 to 12 carbon atoms, $R^2$ represents a single bond or an alkylene group containing from 1 to 5 carbon atoms, $R^3$ represents a hydrogen atom, an alkyl or alkoxy group containing from 1 to 8 carbon atoms, a cycloalkyl or cycloalkyloxy group containing from 4 to 7 carbon atoms and being unsubstituted or substituted by at least one alkyl group containing from 1 to 8 carbon atoms, or a phenyl or phenoxy group unsubstituted or substituted by at least one halogen atom, trifluoromethyl group or alkyl group containing from 1 to 4 carbon atoms one of $R^4$ and $R^5$ represents a hydrogen atom and the other represents a hydroxy group or $R^4$ and $R^5$ together represent an oxo group, $R^6$ represents a hydrogen atom or a hydroxy-protecting group which may be removed under acidic conditions, the double bond between the carbon atoms in positions 13 and 14 is in trans (i.e. E)-configuration, the wavy line ∿ attached to the carbon atom in position 15 represents α- or β-configuration (i.e. S- or R-configuration) or a mixture thereof and, when one of $R^4$ and $R^5$ represents a hydrogen atom and the other represents a hydroxy group, the configuration of the carbon atom in position 3 is R— or S or a mixture thereof (i.e. RS), provided that, when $R^2$ represents a single bond, $R^3$ does not represent an alkoxy group, a cycloalkyloxy group or a phenoxy group] and, when $R^6$ represents a hydrogen atom, cyclodextrin clathrates thereof, and, when $R^1$ and $R^6$ represent hydrogen atoms, nontoxic salts thereof. When the symbols $R^6$ in formula IV represent hydroxy-protecting groups which may be removed under acidic conditions those groups may be the same or different.

The present invention is concerned with all compounds of general formula IV in the optically active "natural" form or its enantiomeric form, or mixtures thereof (particularly the racemic form consisting of equimolecular mixtures of "natural" form and its enantiomeric form).

As will be apparent to those skilled in the art, the compounds of general formula IV have at least four centres of chirality, these four centres of chirality being at the C-8, C-11, C-12, and C-15 carbon atoms. Further centres of chirality may occur when the alkyl and alkylene groups represented by $R^1$, $R^2$ or $R^3$ are branched-chain or when one of $R^4$ and $R^5$ represents a hydrogen atom and the other represents a hydroxy group. The presence of chirality leads, as is well known, to the existence of isomerism. However, the compounds of general formula IV all have such a configuration that the side-chains attached to the alicyclic ring carbon atoms in the positions identified as 8 and 12 are trans with respect to each other. Accordingly, all isomers of general formula IV and mixtures thereof which have those substituent groups attached to the ring carbon atoms in positions 8 and 12 in the trans-configuration and have a hydroxy group as depicted in the 15 position are to be considered within the scope of general formula IV.

In this specification, it is to be understood that the alkyl and alkylene groups, and the alkyl and alkylene moieties may be straight- or branched-chain. It is also to be understood that double bonds depicted between the carbon atoms in positions 13 and 14 are all trans.

Examples of the $C_1$ to $C_{12}$ alkyl groups represented by $R^1$ are methyl, ethyl, propyl, butyl, pentyl, hexyl, heptyl, octyl, nonyl, decyl, undecyl, dodecyl, and isomers thereof. Preferably, $R^1$ represents a hydrogen atom or an alkyl group containing from 1 to 4 carbon atoms, i.e. methyl, ethyl, propyl, isopropyl, butyl, isobutyl, sec-butyl or tert-butyl; most preferably $R^1$ represents a hydrogen atom or a methyl group.

Examples of the group —$R^2$—$R^3$ are methyl, ethyl, 1-methylethyl, propyl, 1-methylpropyl, 2-methylpropyl, 1-ethylpropyl, butyl, 1-methylbutyl, 2-methylbutyl, 3-methylbutyl, 1-ethylbutyl, 2-ethylbutyl, pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, hexyl, 1-methylhexyl, 2-methylhexyl, 1,1-dimethylhexyl, 1-ethylhexyl, 2-ethylhexyl, heptyl, 2-ethylheptyl, nonyl, undecyl, cyclobutyl, 1-propylcyclobutyl, 1-butylcyclobutyl, 1-pentylcyclobutyl, 1-hexylcyclobutyl, 2-methylcyclobutyl, 2-propylcyclobutyl, 3-ethylcyclobutyl, 3-propylcyclobutyl, 2,3,4-triethylcyclobutyl, cyclopentyl, cyclopentylmethyl, 1-cyclopentylethyl, 2-cyclopentylethyl, 2-cyclopentylpropyl, 3-cyclopentylpropyl, 2-pentylcyclopentyl, 2,2-dimethylcyclopentyl, 3-ethylcyclopentyl, 3-propylcyclopentyl, 3-butylcyclopentyl, 3-tert-butylcyclopentyl, (1-methyl-3-propyl)cyclopentyl, (2-methyl-3-propyl)cyclopentyl, (2-methyl-4-propyl)cyclopentyl, cyclohexyl, cyclohexylmethyl, 1-cyclohexylethyl, 2-cyclohexylethyl, 3-cyclohexylpropyl, (1-methyl-2-cyclohexyl)ethyl, 2-cyclohexylpropyl, (1-methyl-1-cyclohexyl)ethyl, 4-cyclohexylbutyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,6-dimethylcyclohexyl, 2,2-dimethylcyclohexyl, (2,6-dimethyl-4-propyl)cyclohexyl, 1-methylcyclohexylmethyl, cycloheptyl, cycloheptylmethyl, 1-cycloheptylethyl, 2-cycloheptylethyl, phenyl, benzyl, 1-phenylethyl, 2-phenylethyl, 3-phenylpropyl, 4-phenylbutyl, 5-phenylpentyl, (1-methyl-2-phenyl)ethyl, (1,1-dimethyl-2-phenyl)ethyl, (1-methyl-1-phenyl)ethyl, 1-phenylpentyl, phenoxymethyl, 2-phenoxyethyl, 3-phenoxypropyl, 4-phenoxybutyl, 5-phenoxypentyl, 3-chlorophenoxymethyl, 4-chlorophenoxymethyl, 4-fluorophenoxymethyl, 3-trifluoromethylphenoxymethyl, 2-methylphenoxymethyl, 3-methylphenoxymethyl, 4-methylphenoxymethyl, 4-ethylphenoxymethyl, 4-tert-butylphenoxymethyl, 4-sec-butylphenoxymethyl, propoxymethyl, isopropoxymethyl, butoxymethyl, pentyloxymethyl, hexyloxymethyl, 1-ethoxyethyl, 1-propoxyethyl, 1-isopropoxyethyl, 1-neopentyloxyethyl, 1-pentyloxyethyl, (1-methyl-1-ethoxy)ethyl, (1-methyl-1-propoxy)ethyl, (1-methyl-1-isobutoxy)ethyl, (1-methyl-1-neopentyloxy)ethyl, (1-methyl-1-butoxy)ethyl, (1-methyl-1-isopentyloxy)ethyl, (1-methyl-1-pentyloxy)ethyl, 2-ethoxyethyl, 2-propoxyethyl, 2-butoxyethyl, 2-(1-ethylbutoxy)ethyl, 2-pentyloxyethyl, 1-ethoxypropyl, 1-propoxypropyl, 1-(2-methylbutoxy)propyl, 1-pentyloxypropyl, 2-methoxypropyl, 3-methoxypropyl, 3-ethoxypropyl, 3-propoxypropyl, 3-sec-butoxypropyl, 3-isobutoxypropyl, 3-butoxypropyl, (1-methyl-2-methoxy)ethyl, (1-methyl-2-ethoxy)ethyl, (1-methyl-2-isobutoxy)ethyl, 1-pentyloxybutyl, (1-pentyloxy-2-methyl)propyl, 4-methoxybutyl, 4-ethoxybutyl, 4-propoxybutyl, (1-methyl-3-methoxy)propyl, (1-methyl-3-propoxy)propyl, (2-methyl-3-methoxy)propyl, (1,1-dimethyl-2ethoxy)ethyl, (1,1-dimethyl-2-propoxy)ethyl, (1,1-dimethyl-2-isobutoxy)ethyl, 5-methoxypentyl, 5-ethoxypentyl, 1-pentyloxypentyl, (1-ethyl-3-propoxy)propyl, cyclobutyloxymethyl, cyclopentyloxymethyl, cyclohexyloxymethyl, cycloheptyloxymethyl, 2-cyclopentyloxyethyl and 2-cyclohexyloxyethyl.

Preferably the grouping —$R^2$—$R^3$ represents n-pentyl or n-hexyl unsubstituted or substituted by one or two methyl group(s), or $R^2$ represents a single bond or a methylene or ethylene group and $R^3$ represents a cyclopentyl or cyclohexyl group unsubstituted or substituted by an alkyl group containing from 1 to 4 carbon atoms, or a phenyl or phenoxy group unsubstituted or substituted by at least one halogen atom or trifluoromethyl group; particularly preferred examples of the grouping —$R^2$—$R^3$ are n-pentyl, 1-methylpentyl, 2-methylpentyl, 1,1-dimethylpentyl, n-hexyl, 2-methylhexyl, cyclopentyl, cyclopentylmethyl, 2-cyclopentylethyl, 3-ethylcyclopentyl, 3-propylcyclopentyl, 3-butylcyclopentyl, cyclohexyl, cyclohexylmethyl, 2-cyclohexylethyl, 4-methylcyclohexyl, 4-propylcyclohexyl, benzyl, 2-phenylethyl, phenoxymethyl, 3-chlorophenoxymethyl, 4-chlorophenoxymethyl and 3-trifluoromethylphenoxymethyl; 1,1-dimethylpentyl is most preferred.

The hydroxy-protecting groups represented by $R^6$ which may be removed under acidic conditions are groups which have no influence on other parts of the compounds during elimination of the protecting groups and which may be easily removed under mild acidic conditions, for example;

(1) a heterocyclic group such as a tetrahydropyran-2-yl, tetrahydrofuran-2-yl or tetrahydrothiopyran-2-yl group;

(2) an ether group such as a 1-ethoxyethyl, 1-methoxy-1-methylethyl, 1-methoxycyclohexyl or 1-methoxy-1-phenylethyl group; and (3) a tri-substituted silyl group such as a trimethylsilyl, triethylsilyl, tributylsilyl, tert-butyldimethylsilyl, tribenzylsilyl or triphenylsilyl group.

Preferably $R^6$ represents a hydrogen atom or a tetrahydropyran-2-yl group.

The wavy line attached to the carbon atom in position 15 is preferably in α-configuration.

According to a feature of the present invention, prostaglandin analogues of general formula IV wherein $R^6$ represents a hydrogen atom and the other symbols are as hereinbefore defined, i.e. compounds of the general formula:

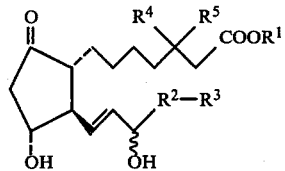

IVA (wherein the various symbols are as hereinbefore defined) are prepared by the conversion to hydroxy groups of the groups $OR^6$ of compounds of general formula IV wherein $R^6$ is other than a hydrogen atom and the other symbols are as hereinbefore defined, i.e. compounds of the general formula:

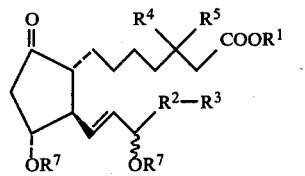

IVB (wherein $R^7$ represents a hydroxy-protecting group which may be removed under acidic conditions, and the other symbols are as hereinbefore defined) under acid conditions. The hydroxy-protecting groups represented by $R^7$ may be the same or different. The groups $OR^7$ may be converted to hydroxy groups by known methods. The conversion is generally carried out under mild acidic conditions. (By the expression "known methods" as used in this specification is meant methods heretofore used or described in the chemical literature). For example, the reaction can be carried out:

(1) at a temperature from ambient to 75° C. in an aqueous solution of an organic acid such as acetic acid, propionic acid, oxalic acid or p-toluenesulphonic acid, or in an aqueous solution of an inorganic acid such as hydrochloric acid, sulphuric acid, or phosphoric acid, preferably in the presence of a water-miscible organic solvent such as an alkanol containing from 1 to 4 carbon atoms (e.g. methanol or ethanol, preferably methanol) or an ether (e.g. 1,2-dimethoxyethane, dioxan or tetrahydrofuran, preferably tetrahydrofuran);

(2) at a temperature from 0° C. to 45° C. in an absolute alkanol containing from 1 to 4 carbon atoms (e.g. absolute methanol or absolute ethanol) in the presence of an organic acid such as p-toluenesulphonic acid or trifluoroacetic acid; or (3) at a temperature from 10° C. to 60° C. in an absolute alkanol containing from 1 to 4 carbon atoms (e.g. absolute methanol or absolute ethanol) in the presence of p-toluenesulphonic acid-pyridine complex or trifluoroacetic acid-pyridine complex.

Preferably, the conversion of the groups $OR^7$ to hydroxy groups is carried out using a mixture of dilute hydrochloric acid and tetrahydrofuran, a mixture of dilute hydrochloric acid and methanol, a mixture of acetic acid, water, and tetrahydrofuran, a mixture of phosphoric acid, water, and tetrahydrofuran, a mixture of p-toluenesulphonic acid and methanol, a mixture of p-toluenesulphonic acid-pyridine complex and methanol, or a mixture of trifluoroacetic acid-pyridine complex and methanol.

Compounds of general formula IVB wherein $R^4$ and $R^5$ together represent an oxo group and the other symbols are as hereinbefore defined, i.e. compounds of the general formula:

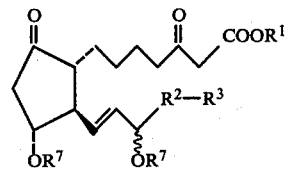

IVC (wherein the various symbols are as hereinbefore defined) can be obtained by oxidising to an oxo group the hydroxy group of compounds of general formula IVB wherein one of $R^4$ and $R^5$ represents a hydrogen atom and the other represents a hydroxy group and the other symbols are as hereinbefore defined, i.e. compounds of the general formula:

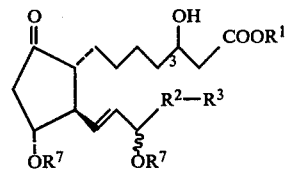

IVD wherein the configuration of the 3-position carbon atom is R— or S, or a mixture thereof (RS), and the various symbols are as hereinbefore defined.

The oxidation of the hydroxy group to an oxo group may be carried out by known methods, for example as described in:

(a) "Synthetic Organic Chemistry III, Organic Synthesis 1", pp. 176–206 (compiled by Tetsuji Kameya and published by Nankodo (Japan) on Aug. 1, 1976) or (b) "Compendium of Organic Synthetic Methods", vol. 1, vol. 2, and vol. 3, section 48 or 168 [published by John Wiley & Sons, Inc. (USA) in 1971, 1974, and 1977, respectively].

The oxidation is preferably carried out under mild neutral conditions using, for example, dimethylsulphide-N-chlorosuccinimide complex, thioanisole-N-chlorosuccinimide complex, dimethylsulphide-chlorine complex, thioanisole-chlorine complex [see J. Amer. Chem. Soc., 94, 7586 (1972) with respect to these complexes], dicyclohexylcarbodiimide-dimethylsulphoxide complex [see J. Amer. Chem. Soc., 87, 5661 (1965)], pyridinium chlorochromate ($C_5H_5NHCrO_3Cl$) [see Tetrahedron Letters, 2647 (1975)], sulphuric anhydride-pyridine complex [see J. Amer. Chem. Soc., 89, 5505 (1967)], chromyl chloride [see. J. Amer. Chem. Soc., 97, 5929 (1975)], chromium trioxide-pyridine complex (for example, Collins' reagent), Jones' reagent or chromic acid solution (prepared from chromium trioxide, manganese sulphate, sulphuric acid, and water).

Oxidation using a dimethylsulphide-N-chlorosuccinimide complex, a thioanisole-N-chlorosuccinimide complex, a dimethylsulphide-chlorine complex or a thioanisole-chlorine complex is carried out by reaction in a halogenated hydrocarbon such as chloroform, methylene chloride or carbon tetrachloride, or in toluene, at a temperature from −30° C. to 0° C., followed by treatment with triethylamine.

Oxidation using a dicyclohexylcarbodiimidedimethylsulphoxide complex is usually carried out in excess dimethylsulphoxide at room temperature in the presence of an acid catalyst such as phosphoric acid, phosphorous acid, cyanoacetic acid, pyridine-phosphoric acid salt or trifluoroacetic acid.

Oxidation using pyridinium chlorochromate is carried out in a halogenated hydrocarbon such as chloroform, methylene chloride or carbon tetrachloride usually at room temperature in the presence or absence of sodium acetate.

Oxidation using a sulphuric anhydride-pyridine complex is usually carried out in dimethylsulphoxide at room temperature in the presence of triethylamine.

Oxidation using chromyl chloride is usually carried out in a halogenated hydrocarbon such as chloroform, methylene chloride or carbon tetrachloride in the presence of tert-butanol and pyridine at a temperature from −30° C. to the reflux temperature of the reaction mixture.

Oxidation using a chromium trioxide-pyridine complex is carried out in a halogenated hydrocarbon such as chloroform, methylene chloride or carbon tetrachloride at a temperature from ambient to 0° C., preferably at 0° C.

Oxidation using Jones' reagent is usually carried out at a temperature not higher than ambient.

Oxidation using a chromic acid solution is usually carried out in diethyl ether at a temperature from −10° to 5° C.

Compounds of general formula IVD can be obtained by reacting compounds of the general formula:

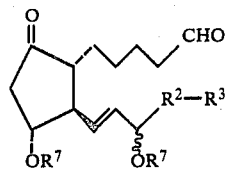

V (wherein the various symbols are as hereinbefore defined) with lithium compounds of the general formula:

$LiCH_2COOR^8$

VI (wherein $R^8$ represents a lithium atom or an alkyl group containing from 1 to 12 carbon atoms), and hydrolysing the product obtained using, for example, an aqueous solution of ammonium chloride, to obtain the compound of general formula IVD.

The reaction is carried out in an inert organic solvent such as tetrahydrofuran, hexamethylphosphoramide (hereinafter abbreviated to HMPA), diethyl ether, hexane, pentane, toluene or a mixture of two or more of them at a temperature not higher than room temperature, preferably from 0° C. to −78° C.

The product of general formula IVD thus obtained is a mixture of isomers in which the hydroxy group at the 3-position is in R- and S-configuration. If desired, the isomer having the hydroxy group in R-configuration may be separated from the isomer having the hydroxy group in S-configuration by known methods, e.g. thin layer, column or high-speed liquid chromatography on silica gel.

Compounds of general formula VI can be obtained by reacting compounds of the general formula:

$CH_3COOR^1$

VII (wherein $R^1$ is as hereinbefore defined) with compounds of the general formula:

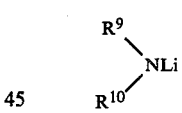

VIII (wherein $R^9$ and $R^{10}$, which may be the same or different, each represents an alkyl group containing from 1 to 6 carbon atoms or a cycloalkyl group containing from 3 to 6 carbon atoms) such as lithium diisopropylamide in an inert organic solvent (for example, tetrahydrofuran, HMPA, diethyl ether, hexane, pentane, or a mixture of two or more of them) at a temperature not higher than room temperature, preferably from 0° C. to −78° C.

Starting materials of general formula V wherein $R^7$ represents a tetrahydropyran-2-yl group and the $OR^7$ group attached to the carbon atom at the 15 position is in α-configuration, i.e. compounds of the general formula:

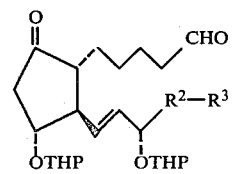

VA (wherein THP represents a tetrahydropyran-2-yl group and the other symbols are as hereinbefore defined) can be prepared by the method described in Japanese Patent Kokai No. 55-100378, British patent application Serial No. 2045745A and French Patent Publication No. 2447374A. Starting materials of general formula V other than compounds of general formula VA may be prepared by obvious modifications of the method described in the above-mentioned published patent specifications.

Cyclodextrin clathrates of compounds of general formula IVA can be prepared by dissolving the cyclodextrin in water or a water-miscible organic solvent, and adding to the solution the prostaglandin analogue in a water-miscible organic solvent. The mixture is then heated and the desired cyclodextrin clathrate is isolated from the resulting solution by concentrating the mixture under reduced pressure, or by cooling and separating the product by filtration or decantation. The ratio of organic solvent to water may be varied according to the solubilities of the starting materials and products. Preferably, the temperature is not allowed to exceed 70° C. during preparation of the cyclodextrin clathrate. $\alpha$-, $\beta$- or $\gamma$-Cyclodextrin, or mixtures thereof, may be used to prepare the cyclodextrin clathrates. Conversion into cyclodextrin clathrates serves to increase the stability of the prostaglandin analogues of general formula IVA.

Compounds of general formula IVA wherein $R^1$ represents a hydrogen atom may, if desired, be converted by known methods into salts. Preferably the salts are non-toxic salts. By the term "non-toxic salts", as used in this specification, is meant salts the cations of which are relatively innocuous to the animal organism when used in therapeutic doses so that the beneficial pharmacological properties of the compounds of general formula IVA are not vitiated by side-effects ascribable to those cations. Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable, (i.e. non-toxic) amine salts. Amines suitable for forming such salts with a carboxylic acid are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing 2 or 3 carbon atoms. Suitable non-toxic amine salts are, e.g., tetraalkylammonium, such as tetramethylammonium, salts, and other organic amine salts such as methylamine salts, ethylamine salts, isopropylamine salts, tert-butylamine salts, dimethylamine salts, cyclopentylamine salts, benzylamine salts, phenethylamine salts, piperidine salts, monoethanolamine salts, diethanolamine salts, lysine salts or arginine salts.

Salts may be prepared from the acids of general formula IVA wherein $R^1$ represents a hydrogen atom, by known methods, for example by reaction of stoichiometric quantities of an acid of general formula IVA and the appropriate base, e.g. an alkali metal or alkaline earth metal hydroxide or carbonate, ammonium hydroxide, ammonia or an organic amine, in a suitable solvent. The salts may be isolated by lyophilisation of the solution or, if sufficiently insoluble in the reaction medium, by filtration, if necessary, after removal of part of the solvent.

The prostaglandin analogues of general formula IVA and cyclodextrin clathrates thereof and, when $R^1$ represents a hydrogen atom, non-toxic salts thereof show, in particular, stimulatory activity on uterine contraction in a selective fashion among the various pharmacological activities which are typical of prostaglandins, and are useful in the termination of pregnancy and induction of labour in pregnant female mammals and in contraception and menstrual regulation in female mammals. In addition to the abovementioned valuable pharmacological property the compounds of general formula IVA and cyclodextrin clathrates thereof and, when $R^1$ represents a hydrogen atom, non-toxic salts thereof, possess relatively weak other prostaglandin-like activities such as hypotensive activity and inhibitory activity on blood platelet aggregation, and diarrhoea-producing activity. For example, in standard laboratory tests, (i) (13E)-(3RS,11$\alpha$,15R)-3,11,15-trihydroxy-9-oxo-16,16-dimethylprost-13-enoic acid (abbreviated to 'ONO-1' hereinafter) and (13E)-(11$\alpha$,15R)-3,9-dioxo-11,15-dihydroxy-16,16-dimethylprost-13-enoic acid methyl ester (abbreviated to 'ONO-2' hereinafter) stimulate uterine contraction in the pregnant female rat when administered intravenously on the 20th day of gestation at a dose of 0.1–0.2 $\mu$g/kg animal body weight, (ii) by intravenous administration to the allobarbital-anaesthetized dog, ONO-1 produces a fall in blood pressure of 6 mmHg and 8 mmHg lasting 4 and 6 minutes at the doses of 10 and 20 $\mu$g/kg animal body weight, respectively, and ONO-2 produces a fall in blood pressure of 18 mmHg and 24 mmHg lasting 15 and 18 minutes at the doses of 10 and 20 $\mu$g/kg animal body weight, respectively, (iii) ONO-1 produces a 50% inhibition of adenosine diphosphate-induced blood platelet aggregation in platelet-rich plasma of rats at the concentration of 32.5 $\mu$g/ml in comparison with controls, and ONO-2 produces a 50% inhibition of adenosine diphosphate-induced blood platelet aggregation in platelet-rich plasma of rats at the concentration of 42.1 $\mu$g/ml in comparison with controls, and (iv) the doses by oral administration of ONO-1 and ONO-2 required to produce diarrhoea in 50% of mice so treated are 5–10 mg/kg animal body weight, respectively.

Compounds of general formula IVB are new and useful intermediates for the preparation of compounds of general formula IVA.

Particularly preferred prostaglandin analogues of the present invention are as follows (the 3-hydroxy compounds may be in the (3RS), (3R) or (3S) configuration): 3-hydroxy-PGE$_1$, 3-hydroxy-16-methyl-PGE$_1$, 3-hydroxy-17-methyl-PGE$_1$, 3-hydroxy-16,16-dimethyl-PGE$_1$, 3-hydroxy-20-methyl-PGE$_1$, 3-hydroxy-17,20-dimethyl-PGE$_1$, 3-hydroxy-15-cyclopentyl-16,17,18,19,20-pentanor-PGE$_1$, 3-hydroxy-16-cyclopentyl-17,18,19,20-tetranor-PGE$_1$, 3-hydroxy-17-cyclopentyl-18,19,20-trinor-PGE$_1$, 3-hydroxy-15-(3-ethyl)-cyclopentyl-16,17,18,19,20-pentanor-PGE$_1$, 3-hydroxy-15-(3-propyl)cyclopentyl-16,17,18,19,20-pentanor-PGE$_1$, 3-hydroxy-15-(3-butyl)cyclopentyl-16,17,18,19,20-pentanor-PGE$_1$, 3-hydroxy-15-cyclohexyl-16,17,18,19,20-pentanor-PGE$_1$, 3-hydroxy-16-cyclohexyl-17,18,19,20-tetranor-PGE$_1$, 3-hydroxy-17-cyclohexyl-18,19,20-trinor-PGE$_1$, 3-hydroxy-15-(4-methyl)cyclohexyl-16,17,18,19,20-pentanor-PGE$_1$, 3-hydroxy-15-(4-propyl)cyclohexyl-16,17,18,19,20-pentanor-PGE$_1$, 3-hydroxy-16-phenyl-17,18,19,20-tetranor-PGE$_1$, 3-hydroxy-17-phenyl-18,19,20-trinor-PGE$_1$, 3-hydroxy-16-phenoxy-17,18,19,20-tetranor-PGE$_1$, 3- hydroxy-16-(3-chlorophenoxy)-17,18,19,20-tetranor-PGE$_1$, 3-hydroxy-16-(4-chlorophenoxy)-17,18,19,20-tetranor-PGE$_1$, 3-hydroxy-16-(3-trifluoromethylphenoxy)-17,18,19,20-tetranor-PGE$_1$, 3-oxo-PGE$_1$, 3-oxo-16-methyl-PGE$_1$, 3-oxo-17-methyl-PGE$_1$, 3-oxo-16,16-dimethyl-PGE$_1$, 3-oxo-20-methyl-PGE$_1$, 3-oxo-17,20-dimethyl-PGE$_1$, 3-oxo-15-cyclopentyl-16,17,18,19,20-pentanor-PGE$_1$, 3-oxo-16-cyclopentyl-17,18,19,20-tetranor-PGE$_1$, 3-oxo-17-cyclopentyl-18,19,20-trinor-PGE$_1$, 3-oxo-15-(3-ethyl)cyclopentyl-16,17,18,19,20-pentanor-PGE$_1$, 3-oxo-15-(3-propyl)cyclopentyl-16,17,18,19,20-pentanor-PGE$_1$,3-oxo-15-(3-butyl)cyclopentyl-16,17,18,19,20-pentanor-PGE$_1$, 3-oxo-15-cyclohexyl-16,17,18,19,20-pentanor-PGE$_1$, 3-oxo-16-cyclohexyl-17,18,19,20-tetranor-PGE$_1$, 3-oxo-17-cyclohexyl-18,19,20-trinor-PGE$_1$, 3-oxo-15-(4-methyl)cyclohexyl-16,17,18,19,20-pentanor-PGE$_1$, 3-oxo-15-(4-propyl)cyclohexyl-16,17,18,19,20-pentanor-PGE$_1$, 3-oxo-16-phenyl-17,18,19,20-tetranor-PGE$_1$, 3-oxo-17-phenyl-18,19,20-trinor-PGE$_1$, 3-oxo-16-phenoxy-17,18,19,20-tetranor-PGE$_1$, 3-oxo-16-(3-chlorophenoxy)-17,18,19,20-tetranor-PGE$_1$, 3-oxo-16-(4-chlorophenoxy)-17,18,19,20-tetranor-PGE$_1$, 3-oxo-16-(3-trifluoromethylphenoxy)-17,18,19,20-tetranor-PGE$_1$, and non-toxic salts thereof, and the corresponding esters and cyclodextrin clathrates of such PGE$_1$ analogues and esters thereof.

The most preferred prostaglandin analogues of the invention are 3RS-hydroxy-16,16-dimethyl-PGE$_1$, 3-oxo-16,16-dimethyl-PGE$_1$ methyl ester and 3-oxo-16,16-dimethyl-PGE$_1$ tert-butyl ester.

The following Examples illustrate the preparation of compounds of the present invention. In the Examples "TLC", "IR", "NMR", and "MS" represent, respectively, "thin layer chromatography", "infrared absorption spectrum", "nuclear magnetic resonance spectrum", and "mass spectrometry". Where solvent ratios are specified in chromatographic separations the ratios are by volume: solvents shown in parenthesis are used as developing solvents. Infrared absorption spectra were measured by the liquid film method; unless otherwise specified the nuclear magnetic resonance spectra were measured in deuterochloroform (CDCl$_3$) solution.

EXAMPLE 1

(13E)-(3RS,11α,15R)-3-Hydroxy-9-oxo-11,15-bis(tetrahydropyran-2-yloxy)-16,16-dimethylprost-13-enoic acid methyl ester Under an atmosphere of nitrogen, 0.59 ml of a 1.7 N solution of butyllithium in hexane was added dropwise to an ice-cooled solution of 154 μl of diisopropylamine in 2 ml of tetrahydrofuran, and the ice-cooled mixture was then stirred for 15 minutes to obtain a solution of lithium diisopropylamide. To the solution obtained were added dropwise 80 μl of methyl acetate in 0.32 ml of tetrahydrofuran at −78° C., and the resulting mixture was stirred for 30 minutes at the same temperature. The solution obtained was added dropwise to a solution of 160 mg of (E)-2α-(4-formylbutyl)-3β-[3R-(tetrahydropyran-2-yloxy)-4,4-dimethyloct-1-enyl]-4α-(tetrahydropyran-2-yloxy)-cyclopentan-1-one (the compound described in Example 11 of published British Patent Application Serial No. 2045745A) in 5 ml of tetrahydrofuran at −78° C., and the mixture was stirred for 2 hours at the same temperature. The reaction solution was poured into a saturated aqueous solution of ammonium chloride and extracted with ethyl acetate. The extract was washed successively with water and a saturated aqueous solution of ammonium chloride, dried over anhydrous magnesium sulphate, and concentrated under reduced pressure. The residue was purified by column chromatography on silica gel using a mixture of cyclohexane and ethyl acetate (4:1) as eluent to obtain 55 mg of the title compound having the following physical characteristics:

TLC (benzene:ethyl acetate=1:1): Rf=0.54;
NMR: δ=5.7–5.4 (2H, m), 4.9–4.5 (2H, m), 3.7 (3H, s), 1.0–0.7 (9H, m);
MS: m/e=481.

The following compounds were obtained in the same manner.

(a) (13E)-(3RS,11α,15R)-3-Hydroxy-9-oxo-11,15-bis(tetrahydropyran-2-yloxy)-16,16-dimethylprost-13-enoic acid tert-butyl ester (prepared using a solution of the aforesaid cyclopentan-1-one compound in toluene and a solution of tert-butyl acetate in hexane):

TLC (benzene:ethyl acetate=2:1): Rf=0.45;
NMR: δ=5.8–5.3 (2H, m), 4.9–4.4 (2H, m), 1.46 (9H, s), 1.0–0.7 (9H, m);
MS: m/e=523.

(b) (13E)-(3RS,11α,15R)-3-Hydroxy-9-oxo-11,15-bis(tetrahydropyran-2-yloxy)-16,16-dimethylprost-13-enoic acid (prepared using a solution of the aforesaid cyclopentan-1-one compound in tetrahydrofuran and a solution of acetic acid in a mixture of tetrahydrofuran and hexamethylphosphoramide):

TLC (chloroform:tetrahydrofuran:acetic acid=20:4:1): Rf=0.46;
IR: ν=3450, 2950, 2870, 1750, 1715, 1470, 1455, 1440, 1205, 1140, 1080, 980 cm$^{-1}$;
NMR: δ=6.25 (2H, broad s), 5.7–5.4 (2H, m), 4.9–4.5 (2H, m), 1.0–0.8 (9H, m);
MS: m/e=464.

EXAMPLE 2

(13E)-(11α,15R)-3,9-Dioxo-11,15-bis-(tetrahydropyran-2-yloxy)-16,16-dimethylprost-13-enoic acid methyl ester Under an atmosphere of nitrogen, 100 mg of chromium trioxide and 0.5 g of infusorial earth were added to 0.162 ml of pyridine in 3 ml of methylene chloride, and the mixture was stirred for 15 minutes at room temperature. 55 mg of the 3-hydroxy compound (prepared as described in Example 1) in 1 ml of methylene chloride were added thereto at 0° C., and the mixture was stirred for 20 minutes at the same temperature. To the reaction solution obtained was added 1 g of sodium bisulphate and, after stirring for 20 minutes at 0° C., the mixture was filtered through a magnesium sulphate layer. The filtrate was concentrated under reduced pressure. The residue obtained was purified by column chromatography on silica gel using a mixture of cyclohexane and ethyl acetate (6:1) as eluent to obtain 42 mg of the title compound having the following physical characteristics:

TLC (benzene:ethyl acetate=1:1): Rf=0.71;
NMR: δ=5.7–5.4 (2H, m), 4.9–4.5 (2H, m), 3.7 (3H, s), 3.4 (2H, s), 1.0–0.7 (9H, m);
MS: m/e=477.

The following compound was obtained in the same manner from the hydroxy compound of Example 1(a).

(a) (13E)-(11α,15R)-3,9-dioxo-11,15-bis(tetrahydropyran-2-yloxy)-16,16-dimethylprost-13-enoic acid tert-butyl ester:

TLC (benzene:ethyl acetate=2:1): Rf=0.69;

NMR: δ=5.8–5.3 (2H, m), 4.9–4.4 (2H, m), 3.32 (2H, s), 1.46 (9H, s), 1.0–0.7 (9H, m);
MS: m/e=518.

EXAMPLE 3

(13E)-(11α,15R)-3,9-Dioxo-11,15-dihydroxy-16,16-dimethylprost-13-enoic acid methyl ester [i.e. 3-oxo-16,16-dimethyl-PGE$_1$ methyl ester]

A mixture of 42 mg of the tetrahydropyran-2-yloxy compound (prepared as described in Example 2), 0.4 ml of 65% v/v aqueous acetic acid, and 4 drops of tetrahydrofuran was stirred for 5 minutes at 80° C. The reaction solution was diluted with ethyl acetate, washed successively with water and a saturated aqueous solution of sodium chloride, dried over anhydrous magnesium sulphate, and concentrated under reduced pressure. The residue obtained was purified by column chromatography on silica gel using a mixture of cyclohexane and ethyl acetate (2:1) as eluent to obtain 12.6 mg of the title compound having the following physical characteristics:
TLC (benzene:ethyl acetate=1:2): Rf=0.16;
IR: ν=3420, 2970, 2940, 2879, 1750, 1730, 1650, 1630, 1440, 1330, 1250, 1160, 1080, 978 cm$^{-1}$;
NMR: δ=6.0–5.3 (2H, m), 4.2–3.6 (5H, m), 3.83 (1H, d), 3.73 (3H, s), 3.42 (2H, s), 1.0–0.7 (9H, m);
MS: m/e=392, 378, 374, 361.

The following compounds were obtained in the same manner from the tetrahydropyran-2-yloxy compound of Example 2(a) and the tetrahydropyran-2-yloxy compound of Example 1(b), respectively.

(a) (13E)-(11α,15R)-3,9-Dioxo-11,15-dihydroxy-16,16-dimethylprost-13-enoic acid tert-butyl ester [i.e. 3-oxo-16,16-dimethyl-PGE$_1$ tert-butyl ester]:
TLC (benzene:ethyl acetate=1:2): Rf=0.33;
NMR: δ=5.8–5.3 (2H, m), 4.2–3.6 (2H, m), 3.32 (2H, s), 1.46 (9H, s), 1.0–0.7 (9H, m);
MS: m/e=378.

(b) (13E)-(3RS,11α,15R)-3,11,15-trihydroxy-9-oxo-16,16-dimethylprost-13-enoic acid [i.e. 3RS-hydroxy-16,16-dimethyl-PGE$_1$]:
TLC (chloroform:tetrahydrofuran:acetic acid=10:2:1): Rf=0.08;
IR: ν=3400, 2940, 2870, 1750, 1710, 1380, 1250, 1165, 1080, 1050 cm$^{-1}$;
NMR (CDCl$_3$-acetone-d$_6$ solution): δ=6.0–5.4 (2H, m), 5.0 (4H, broad s), 4.3–3.5 (3H, m), 3.84 (1H, d), 2.74 (1H, dd), 2.6–2.3 (2H, m), 1.0–0.8 (9H, m);
MS: m/e=380, 362, 299, 281.

The present invention includes within its scope pharmaceutical compositions which comprise at least one compound of general formula IVA, cyclodextrin clathrate thereof or, when R$^1$ represents a hydrogen atom, non-toxic salt thereof together with a pharmaceutical carrier or coating. In clinical practice, the compounds of general formula IVA and salts and clathrates thereof will normally be administered orally, intravaginally, intrarectally or parenterally.

Solid compositions for oral administration include compressed tablets, pills, dispersible powders, and granules. In such solid compositions, one or more of the active ingredients is or are admixed with at least one inert diluent such as calcium carbonate, potato starch, dextrin, alginic acid, lactose, mannitol, glucose or cacao butter. The compositions may also comprise, as is normal practice, additional substances other than inert diluents, e.g. lubricating agents, such as magnesium stearate. If desired, tablets or pills may be coated with sugar or gelatin, an enteric substance or film, or with two or more such layers.

Liquid compositions for oral administration include pharmaceutically acceptable emulsions, solutions, suspensions, syrups and elixirs, containing inert diluents commonly used in the art, such as water or liquid paraffin. Besides inert diluents such compositions may also comprise adjuvants, e.g. wetting agents and suspending agents, and sweetening, flavouring, perfuming and preserving agents.

Compositions according to the present invention for oral administration also include capsules of an absorbable material such as gelatin containing one or more of the active compounds with or without the addition of diluents or excipients.

Solid compositions for intrarectal administration include suppositories formulated in manner known per se and containing one or more of the active compounds.

Solid or ointment compositions for intravaginal administration include pessaries, e.g. silicone rubber pessaries, and ointments which comprise one or more carriers, diluents or supports (e.g. cacao butter, macrogol, Witepsol, silicone rubber or Vaseline) containing one or more of the active ingredients and which are formulated according to methods known per se. "Witepsol" and "Vaseline" are registered Trade Marks. Particularly preferred compositions for intravaginal administration are film compositions, formulated in manner known per se, which comprise one or more of the active compounds, and as support, one or more water-soluble polymers (for example, hydroxypropyl cellulose, polyvinyl pyrrolidone, hydroxypropylmethyl cellulose, and polyacrylic acid) and/or water-insoluble polymers (for example, cellulose acetate and polyvinyl acetate), one or more plasticisers, for example, diethyl phthalate, dibutyl phthalate, butyl phthalylbutyl glycolate, diethylene glycol, triethylene glycol, dipropylene glycol, polyethylene glycol, glycerol, diacetin, triacetin, tributyrin or Myvacet and, if desired, one or more organic acids or anhydrides (for example citric acid, citric anhydride, tartaric acid, tartaric anhydride, succinic acid, stearic acid, or palmitic acid). "Myvacet" is a registered Trade Mark.

Preparations according to the present invention for parenteral administration include sterile aqueous or non-aqueous solutions, suspensions and emulsions. Examples of non-aqueous solvents or suspending media are propylene glycol, polyethylene glycol, ethanol, vegetable oils (e.g. olive oil), and injectable organic acid esters (e.g. ethyl oleate and sorbitan esters). These compositions may also include adjuvants such as preserving, wetting, emulsifying and dispersing agents. They may be sterilised, for example, by filtration through a bacteria-retaining filter, by incorporation of sterilising agents in the compositions, or by irradiation. They may also be manufactured in the form of sterile solid compositions, which can be dissolved in sterile water or some other sterile injectable medium immediately before use.

The percentage of active ingredient in the compositions of the present invention may be varied, it being necessary that it should constitute a proportion such that a suitable dosage for the desired therapeutic effect shall be obtained. Several unit dosage forms may of course be administered at the same time. In general the preparations should normally contain at least 0.025% by weight of active substance when required for administration by injection; for oral administration the preparations will normally contain at least 0.1 wt % of active substance.

The dosage employed depends upon, for example, the desired therapeutic effect, the route of administration, the duration of the treatment, age and body weight.

In the human adult, the doses per person are generally between 5 μg and 5 mg by oral, intravaginal, intrauterine, intrarectal, intravenous, intramuscular or extraovular administration for contraception and menstrual regulation in women or in the termination of pregnancy and induction of labour in pregnant women. In domestic female mammals such as cows, mares, sows, ewes and bitches, the doses are generally between 0.001 and 50 mg per animal by intramuscular, subcutaneous, intrauterine, intravaginal or intravenous administration in the induction of abortion and labour.

The following Examples illustrate pharmaceutical compositions of the present invention.

EXAMPLE 4

1000 Tablets containing 0.5 mg of active ingredient per tablet were obtained in a conventional manner from 500 mg of (13E)-(11α,15R)-3,9-dioxo-11,15-dihydroxy-16,16-dimethylprost-13-enoic acid methyl ester, 2 g of carboxymethyl cellulose calcium salt, 0.2 g of silicon dioxide, 2 g of magnesium stearate, and 95.3 g of mannitol.

EXAMPLE 5

100 Pessaries containing 1 mg of active ingredient per pessary were obtained in a conventional manner from 100 mg of (13E)-(11α,15R)-3,9-dioxo-11,15-dihydroxy-16,16-dimethylprost-13-enoic acid methyl ester, 2 ml of ethanol, and 80 g of Witepsol S-52.

EXAMPLE 6

50 Silicone rubber pessaries containing 1 mg of active ingredient per silicone rubber pessary were obtained in a conventional manner from 50 mg of (13E)-(11α,15R)-3,9-dioxo-11,15-dihydroxy-16,16-dimethylprost-13-enoic acid methyl ester, 10 ml of ethanol, 100 sheets of silicone rubber (0.25 mm in thickness and 10 cm² in area), and gelatin (as an adhesive).

EXAMPLE 7

A film composition was prepared in a conventional manner from 0.2 mg of (13E)-(11α,15R)-3,9-dioxo-11,15-dihydroxy-16,16-dimethylprost-13-enoic acid methyl ester, 199.5 mg of hydroxypropyl cellulose, 0.3 mg of citric anhydride, and 3 ml of methanol.

EXAMPLE 8

A film composition was prepared in a conventional manner from 0.2 mg of (13E)-(11α,15R)-3,9-dioxo-11,15-dihydroxy-16,16-dimethylprost-13-enoic acid methyl ester, 20 mg of polyvinyl acetate, 10 mg of glycerol, 10 mg of triacetin, 160 mg of hydroxypropyl cellulose, 0.3 mg of tartaric anhydride, and 3 ml of methanol.

EXAMPLE 9

By proceeding as described in each of Examples 4 to 8 but using (13E)-(3RS,11α,15R)-3,11,15-trihydroxy-9-oxo-16,16-dimethylprost-13-enoic acid in place of (13E)-(11α,15R)-3,9-dioxo-11,15-dihydroxy-16,16-dimethylprost-13-enoic acid methyl ester, there were obtained pharmaceutical compositions corresponding to each of Examples 4 to 8 containing the former compound.

We claim:
1. A prostaglandin analogue of the formula:

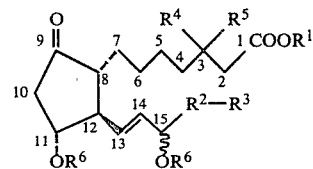

(wherein $R^1$ represents a hydrogen atom or an alkyl group containing from 1 to 12 carbon atoms, $R^2$ represents a single bond or an alkylene group containing from 1 to 5 carbon atoms, $R^3$ represents a hydrogen atom, an alkyl or alkoxy group containing from 1 to 8 carbon atoms, a cycloalkyl or cycloalkyloxy group containing from 4 to 7 carbon atoms and being unsubstituted or substituted by at least one alkyl group containing from 1 to 8 carbon atoms, or a phenyl or phenoxy group unsubstituted or substituted by at least one halogen atom, trifluoromethyl group or alkyl group containing from 1 to 4 carbon atoms, one of $R^4$ and $R^5$ represents a hydrogen atom and the other represents a hydroxy group or $R^4$ and $R^5$ together represent an oxo group, $R^6$ represents a hydrogen atom or a hydroxy-protecting group which may be removed under mild acidic conditions, the double bond between the carbon atoms in positions 13 and 14 is in trans configuration, the wavy line ∼∼ attached to the carbon atom in position 15 represents α- or β-configuration or a mixture thereof and, when one of $R^4$ and $R^5$ represents a hydrogen atom and the other represent a hydroxy group, the configuration of the carbon atom in position 3 is R or S or a mixture thereof, provided that, when $R^2$ represents a single bond, $R^3$ does not represent an alkoxy group, a cycloalkyloxy group or a phenoxy group) or when $R^6$ represents a hydrogen atom, a cyclodextrin clathrate thereof or, when $R^1$ and $R^6$ represent hydrogen atoms, a non-toxic salt thereof.

2. A prostaglandin analogue according to claim 1 wherein $R^6$ represents a hydrogen atom.

3. A prostaglandin analogue according to claim 1 wherein $R^1$ represents a hydrogen atom or a straight- or branched-chain alkyl group containing from 1 to 4 carbon atoms.

4. A prostaglandin analogue according to claim 1 wherein $R^1$ represents a hydrogen atom or a methyl group.

5. A prostaglandin analogue according to claim 1 wherein the grouping —$R^2$—$R^3$ represents n-pentyl or n-hexyl unsubstituted or substituted by one or two methyl group(s), or $R^2$ represents a single bond or a methylene or ethylene group and $R^3$ represents a cyclopentyl or cyclohexyl group unsubstituted or substituted by an alkyl group containing from 1 to 4 four carbon atoms, or a phenyl or phenoxy group unsubstituted or substituted by at least one halogen atom or trifluoromethyl group.

6. A prostaglandin analogue according to claim 1 wherein the grouping —$R^2$—$R^3$ represents n-pentyl, 1-methylpentyl, 2-methylpentyl, 1,1-dimethylpentyl, n-hexyl, 2-methylhexyl, cyclopentyl, cyclopentylmethyl, 2-cyclopentylethyl, 3-ethylcyclopentyl, 3-propylcyclopentyl, 3-butylcyclopentyl, cyclohexyl, cyclohexylmethyl, 2-cyclohexylethyl, 4-methylcyclohexyl, 4-propylcyclohexyl, benzyl, 2-phenylethyl, phenoxymethyl, 3-chlorophenoxymethyl, 4-chlorophenoxymethyl or 3-trifluoromethylphenoxymethyl.

7. A prostaglandin analogue according to claim 1 wherein the grouping —$R^2$—$R^3$ represents 1,1-dimethylpentyl.

8. A prostaglandin analogue according to claim 1 wherein the group $OR^6$ attached to the C-15 carbon atoms in formula IV depicted in claim 1 is in α-configuration.

9. A compound according to claim 1 which is (13E)-(11α,15R)-3,9-dioxo-11,15-dihydroxy-16,16-dimethylprost-13-enoic acid methyl ester or a cyclodextrin clathrate thereof.

10. A compound according to claim 1 which is (13E)-(11α,15R)-3,9-dioxo-11,15-dihydroxy-16,16-dimethylprost-13-enoic acid tert-butyl ester or a cyclodextrin clathrate thereof.

11. A compound according to claim 1 which is (13E)-(3RS,11α,15R)-3,11,15-trihydroxy-9-oxo-16,16-dimethylprost-13-enoic acid or a cyclodextrin clathrate or non-toxic salt thereof.

12. A compound according to claim 1 which is a non-toxic salt of a prostaglandin analogue as claimed in any one of claims 1 to 8 wherein $R^1$ and $R^6$ both represent hydrogen atoms.

13. A compound according to claim 1 which is a cyclodextrin clathrate of a prostaglandin analogue as claimed in any one of claims 1 to 8 wherein $R^6$ represents a hydrogen atom.

14. A pharmaceutical composition useful in the termination of pregnancy or induction of labour in pregnant female mammals and in contraception and menstrual regulation in female mammals which comprises an effective amount of at least one compound of general formula IV claimed in claim 1, wherein $R^6$ represents a hydrogen atom and the other symbols are as defined in claim 1, or cyclodextrin clathrate thereof, or when $R^1$ represents a hydrogen atom, non-toxic salt thereof, in association with a pharmaceutical carrier or coating.

15. A pharmaceutical composition according to claim 14 in which the active ingredient is (13E)-(11α,15R)-3,9-dioxo-11,15-dihydroxy-16,16-dimethylprost-13-enoic acid methyl ester or (13E)-(11α,15R)-3,9-dioxo-11,15-dihydroxy-16,16-dimethylprost-13-enoic acid tert-butyl ester or a cyclodextrin clathrate thereof, or (13E)-(3RS,11α,15R)-3,11,15-trihydroxy-9-oxo-16,16-dimethylprost-13-enoic acid or a non-toxic salt or cyclodextrin clathrate thereof.

16. A method for the termination of pregnancy or induction of labour in a pregnant female mammal or for contraception or menstrual regulation in a female mammal which comprises administering an effective amount of a compound of general formula IV claimed in claim 1 wherein $R^6$ represents a hydrogen atom, and the other symbols are as defined in claim 1, or of a cyclodextrin clathrate thereof or, when $R^1$ represents a hydrogen atom, of a nontoxic salt thereof.

17. A prostaglandin analogue according to claim 1 wherein $R^6$ represents a hydroxy-protecting group which may be removed under mild acidic conditions and the other symbols are as defined in claim 1.

18. A compound according to claim 1 which is (13E)-(11α,15R)-3,9-dioxo-11,15-bis(tetrahydropyran-2-yloxy)-16,16-dimethylprost-13-enoic acid methyl ester.

19. A compound according to claim 1 which is (13E)-(11α,15R)-3,9-dioxo-11,15-bis(tetrahydropyran-2-yloxy)-16,16-dimethylprost-13-enoic acid tert-butyl ester.

20. A compound according to claim 1 which is (13E)-(3RS,11α,15R)-3-hydroxy-9-oxo-11,15-bis(tetrahydropyran-2-yloxy)-16,16-dimethylprost-13-enoic acid methyl ester.

21. A compound according to claim 1 which is (13E)-(3RS,11α,15R)-3-hydroxy-9-oxo-11,15-bis(tetrahydropyran-2-yloxy)-16,16-dimethylprost-13-enoic acid tert-butyl ester.

22. A compound according to claim 1 which is (13E)-(3RS,11α,15R)-3-hydroxy-9-oxo-11,15-bis(tetrahydropyran-2-yloxy)-16,16-dimethylprost-13-enoic acid.

* * * * *